United States Patent
Cappello et al.

(10) Patent No.: US 11,021,382 B2
(45) Date of Patent: Jun. 1, 2021

(54) METHODS FOR BIOREMEDIATION OF WATERS CONTAMINATED WITH HYDROCARBONS

(71) Applicant: BIO-ON S.p.A., San Giorgio di Piano (IT)

(72) Inventors: Simone Cappello, Naples (IT); Simone Begotti, San Giorgio di Piano (IT); Lucrezia Genovese, Naples (IT)

(73) Assignee: BIO-ON S.P.A., San Giorgio di Piano (IT)

( * ) Notice: Subject to any disclaimer, the term of this patent is extended or adjusted under 35 U.S.C. 154(b) by 0 days.

(21) Appl. No.: 16/335,841

(22) PCT Filed: Sep. 25, 2017

(86) PCT No.: PCT/IB2017/055803
§ 371 (c)(1),
(2) Date: Mar. 22, 2019

(87) PCT Pub. No.: WO2018/055587
PCT Pub. Date: Mar. 29, 2018

(65) Prior Publication Data
US 2020/0024172 A1    Jan. 23, 2020

(30) Foreign Application Priority Data
Sep. 26, 2016 (IT) .................. 102016000096370

(51) Int. Cl.
C02F 3/34      (2006.01)
C02F 3/02      (2006.01)
(Continued)

(52) U.S. Cl.
CPC ............... C02F 3/344 (2013.01); A62D 3/02 (2013.01); B09C 1/08 (2013.01); B09C 1/10 (2013.01);
(Continued)

(58) Field of Classification Search
CPC .................... C02F 5/125; C02F 2101/10; C02F 2103/007; C02F 2103/08; C02F 2303/22;
(Continued)

(56) References Cited

U.S. PATENT DOCUMENTS 8,956,835 B2    2/2015   Nakas et al.
2015/0337344 A1  11/2015  Albuquerque et al.

FOREIGN PATENT DOCUMENTS

CN    101928069 A    12/2010
CN    101928188 A    12/2010
(Continued)

OTHER PUBLICATIONS

Machine-generated English Translation of JP 2014-132831, dated Jan. 15, 2020.*
(Continued)

*Primary Examiner* — Fred Prince
(74) *Attorney, Agent, or Firm* — MH2 Technology Law Group, LLP

(57) ABSTRACT

A method for bioremediation of waters contaminated with hydrocarbons may include: putting the contaminated waters in contact with at least one polyhydroxyalkanoate (PHA); and/or allowing microorganisms, present in the contaminated waters and capable of metabolizing the hydrocarbons, to develop and degrade the hydrocarbons under an aerobic condition.

20 Claims, 2 Drawing Sheets

Figure 1:
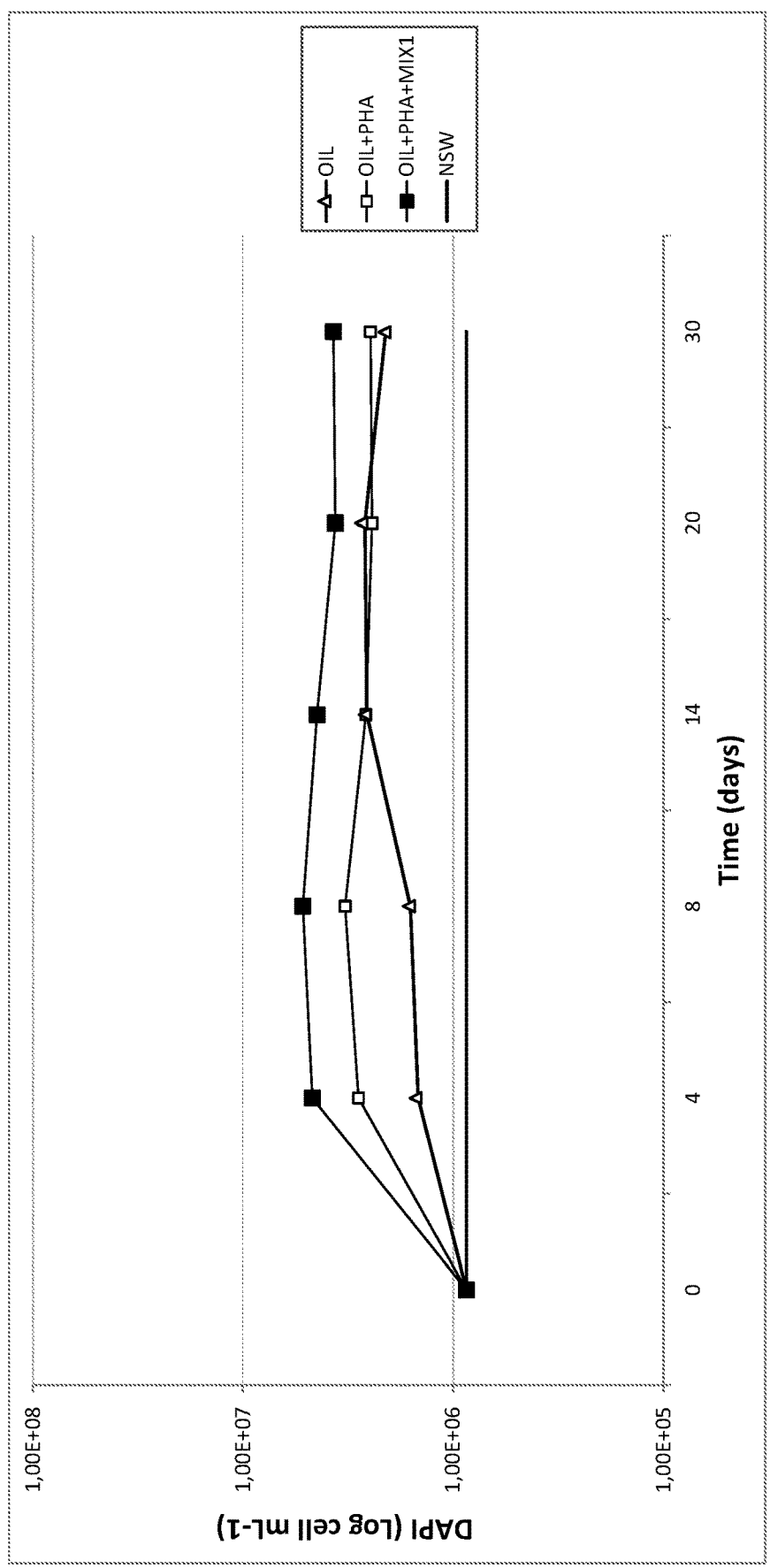

(51) Int. Cl.
  *B09C 1/08* (2006.01)
  *B09C 1/10* (2006.01)
  *A62D 3/02* (2007.01)
  *C02F 101/32* (2006.01)
  *C02F 103/08* (2006.01)

(52) U.S. Cl.
  CPC ...... *C02F 2101/32* (2013.01); *C02F 2103/08* (2013.01); *C02F 2305/04* (2013.01)

(58) Field of Classification Search
  CPC .... C02F 2307/10; C02F 2307/12; C02F 5/10; C02F 1/42; C02F 3/104; C02F 3/108; C02F 3/342; C02F 2103/023; B01J 31/06; B01J 31/003; Y02W 10/15; C12Y 402/01001; C12N 9/0004; C12N 9/14; C12N 9/88; C12N 11/08; C12N 11/02; C12N 9/004
  USPC .................................. 210/601, 610, 611, 631
  See application file for complete search history.

(56) References Cited

FOREIGN PATENT DOCUMENTS

| | | |
|---|---|---|
| JP | 2005334727 A | 12/2005 |
| JP | 2014132831 A | 7/2014 |
| WO | 1999/023146 A1 | 5/1999 |
| WO | 2011/045625 A1 | 4/2011 |
| WO | 2013/149662 A1 | 10/2013 |
| WO | 2015/015315 A2 | 2/2015 |
| WO | 2015/015395 A1 | 2/2015 |

OTHER PUBLICATIONS

Machine-generated English Translation of JP 2005-334727, dated Jan. 16, 2020.*
Aulenta et al., "Use of poly-β-hydroxy-butyrate as a slow-release electron donor for the microbial reductive dechlorination of TCE," Water Science & Technology (2008) 57, 6, pp. 921-925.
International Search Report and the Written Opinion of the International Searching Authority dated Feb. 7, 2018, of corresponding PCT Application No. PCT/IB2017/055803 (12 pages).

* cited by examiner

METHODS FOR BIOREMEDIATION OF WATERS CONTAMINATED WITH HYDROCARBONS

CROSS-REFERENCE TO RELATED APPLICATION(S)

This application is a national stage entry from International Application No. PCT/M2017/055803, filed on Sep. 25, 2017, in the Receiving Office ("RO/IB") of the International Bureau of the World Intellectual Property Organization ("WIPO"), published as International Publication No. WO 2018/055587 A1 on Mar. 29, 2018; International Application No. PCT/IB2017/055803 claims priority under 35 U.S.C. § 119 from Italian Patent Application No. 102016000096370, filed on Sep. 26, 2016, in the Italian Patent and Trademark Office ("IPTO"), the entire contents of all of which are incorporated herein by reference.

The present invention relates to a method for the bioremediation of waters contaminated with hydrocarbons, comprising the use of a composition based on a biodegradable polymer.

It is known that numerous microorganisms, in particular bacteria, are capable of metabolizing a large number of polluting substances which can be present in a body of water due to the spillage of various kinds of chemical substances, in particular hydrocarbon substances of a petroleum origin. These microorganisms degrade these substances through metabolic processes of the oxidative type until water and carbon dioxide are obtained. Processes for the remediation of polluted waters, known as bioremediation, are based on this natural effect.

Bioremediation, however, is often quite ineffective, mainly due to the low quantity of microorganisms present in the environment that are capable of causing degradation in an acceptable time or under the environmental conditions of the site to be remediated, not optimal for bacterial growth.

In some cases, it is therefore advantageous to effect a so-called biostimulation of the site to be remediated, which comprises applying stimulation techniques of the growth rates of natural microbial communities having biodegradation capabilities by the addition of nutrients, in organic and/or inorganic form.

In a marine environment, the bacterial growth is generally limited by the low concentration of nutrients, normally represented by nitrogen and phosphorous compounds. Marine ecosystems are in fact, for biotic and abiotic reasons, generally lacking in these substances, which can undergo a strong "uptake" on the part of microorganisms that do not degrade crude oil (also including phytoplankton).

In order to support the growth of autochthonous populations of bacteria capable of degrading hydrocarbons, one of the techniques most widely adopted during bioremediation processes is the use of fertilizers as nutritional source, for example soluble nitrogen-based fertilizers, slow-release fertilizers (SFRs) or oleophilic fertilizers. Another supply of nutrients can be provided by the introduction of water-soluble nutrients such as mineral salts (for example $KNO_3$, $NaNO_3$, $NH_4NO_3$, $K_2HPO_4$, $MgNH_4PO_4$) and commercial inorganic fertilizers.

If compared with other nutrients (for example oleophilic nutrients), water-soluble nutrients are more readily available for the microbial metabolism. Due to their soluble nature, however, they have the main drawback of being more readily diluted and dispersed by the action of waves and tides.

In order to enhance the bioremediation process, it is also possible to effect a so-called bio-augmentation, which consists in adding to the system to be remediated, large densities of bacterial populations (single bacteria or microbial consortia) with particular catabolic abilities, to integrate the indigenous population in order to accelerate or activate the degradation of polluting substances. According to some studies, bioaugmentation has proved to be extremely effective for the remediation of polycyclic aromatic hydrocarbons (IPA) in sediments with little or no potential for intrinsic degradation, whereas other studies have demonstrated that this technique does not significantly improve what may be natural attenuation.

A problem observed in the application of bioaugmentation is that of guaranteeing the survival and activity of the organisms introduced into the environment. Furthermore, the bioaugmentation can be inhibited by various factors, among which the pH and the presence of products with a high redox potential and toxic pollutants, the concentration and bio-availability of contaminants or the absence of specific substrates. The key factor for considering for the success of this technique, however, is definitely the choice of the strain and/or bacterial consortium, which must take into account the type of community present in the environment considered.

Bioaugmentation strategies can prove to be effective above all in the remediation of contaminants of an anthropic origin, where specialized bacteria with the appropriate catabolic pathways may not be present in the contaminated environment. The selection of bioaugmentation as remediation strategy becomes important if the limiting factor of natural biodegradation processes is the absence of specific catabolic genes in the indigenous microbial community. This lack of genetic information will be therefore completed by the strain introduced.

With respect to the microorganisms present in the environment, which are capable of degrading hydrocarbons, these are normally bacteria which are known as hydrocarbon-degrading bacteria or oil-eating bacteria (BICs). A single bacterial species is capable of degrading only a limited number of oil compounds, whereas a consortium composed of various bacterial species (with different enzymatic features) can develop a metabolic syntropy which can lead to a complete mineralization of the hydrocarbons up to the production of $CO_2$ and $H_2O$. The capacity of degrading oil hydrocarbons is not restricted to a few microorganisms: over 30 kinds of marine bacteria have been identified and distributed in different (sub)phyla ($\alpha$-, $\beta$-, $\gamma$-Proteobacteria; Gram positive; Flexibacter-Cytophaga-Bacteroides). Among the most important types (based on the frequency of isolation) the following can be mentioned: *Pseudomonas, Achromobacter, Nocardia, Micrococcus, Vibrio, Acinetobacter, Brevibacter, Flavobacterium.*

In addition to these heterotrophic bacteria (i.e. capable of using alternative carbon sources in addition to hydrocarbon sources), a new series of hydrocarbon-degrading marine bacteria have been isolated through different culture methods containing hydrocarbons as sole carbon source and subsequent taxonomic and physiological analysis, characterized by a slow growth under oligotrophic conditions, which have proved to be competent in using exclusively petroleum hydrocarbons with the sole source of carbon and energy.

An analysis of the gene sequence of 16S rRNA reveals that these BICs often prove to be correlated with *Marinomonas vaga, Oceanospirillum linum* and *Halomonas elongate* belonging to the group of $\gamma$-Proteobacteria.

With reference to their metabolic properties, these can be subdivided into two groups, those that degrade aliphatic hydrocarbons and those that degrade aromatic hydrocarbons. *Alcanivorax borkumensis* (isolated from the North Sea), *Alcanivorax* sp. ST1 (sea of Japan), *Marinobacter hydrocarbonoclasticus* (Mediterranean sea) and *Marinobacter* sp. CAB (Mediterranean sea) degrade linear or branched aliphatic chains, whereas bacteria such as *Cycloclasticus oligotrophus, C. pugetii* and *Psychroserpens burtonensis* use aromatic hydrocarbons such as toluene, naphthalene, phenanthrene and anthracene as sole carbon source.

BICs occupy a unique trophic niche among heterotrophic bacteria that participate in the global carbon cycle, as they preferably consume aliphatic and aromatic hydrocarbons which are relatively difficult to use for normal autotrophic and heterotrophic microbial flora present in the environment. As these bacteria have unusual physiological features, they also have few rRNA operons (1 or 2), few cytoplasmic proteins (not more than 300) and a small genome (3-4 Mbp). Furthermore, the number of membrane proteins is 1.5-2 times lower than other heterotrophic bacteria such as *E. coli* or *Pseudomonas*, and this can probably be explained by the fact that the cells can only use some substrates.

The Applicant has considered the problem of increasing the effectiveness of bioremediation processes through the supply of substances that can in some way favour the development of aerobic microorganisms capable of metabolizing hydrocarbons, without supplying non-biodegradable materials which would have to be removed after the treatment, making the process complex and expensive and not without risks from an environmental point of view.

This problem and others which will be described in greater detail hereunder, have been solved by putting waters contaminated with hydrocarbons in contact with a poly-hydroxyalkanoate (PHA), a highly biodegradable polymeric material which the Applicant has verified as being surprisingly capable of stimulating, alone, without the addition of other substances, the metabolic activity of aerobic microorganisms capable of metabolizing hydrocarbons. By allowing these microorganisms to act on hydrocarbons under an aerobic condition, a significant reduction in environmental pollution is obtained in relatively short times, without introducing extraneous non-biodegradable materials into the environment.

Furthermore, the Applicant has found that a further increase in the bioremediation activity can be obtained by adding to the PHA, at least one nutritive substance for microorganisms and/or at least one microorganism capable of metabolizing hydrocarbons, thanks to the fact that the PHA acts as a support for said substances and/or microorganisms, so as to guarantee their permanence in the ecological niche where the hydrocarbon spill is present.

According to a first aspect, the present invention therefore relates to a method for the bioremediation of waters contaminated with hydrocarbons, which comprises:
putting said contaminated waters in contact with at least one poly-hydroxyalkanoate (PHA);
allowing the microorganisms present in said contaminated waters and capable of metabolizing hydrocarbons, to develop and degrade the hydrocarbons under an aerobic condition.

Said PHA is preferably dispersed in the contaminated waters in the form of particles, in particular in the form of powder or microgranules.

Said PHA also preferably comprises at least one nutritive substance suitable for favouring the development of microorganisms.

Said PHA also preferably comprises at least one microorganism capable of metabolizing hydrocarbons. Such metabolic ability can be total, i.e. with the complete degradation of the hydrocarbons, or partial.

Without the intention of being bound to an interpretative theory of the present invention, the fact that PHA is surprisingly capable of stimulating, alone, without the addition of other substances, the metabolic activity of microorganisms capable of metabolizing hydrocarbons, can be due to the highly biodegradable nature of PHA itself, which is produced through a fermentation process of organic substrates and is thus akin to microorganisms in general, in particular to hydrocarbon-degrading bacteria and/or to oil-eating bacteria (BICs).

Furthermore, the use of PHA as a support for bacteria and/or nutritive substances of the same, in particular allows the bioremediation effect to be prolonged in the ecological niche within which the hydrocarbon spill has occurred. PHA is in fact a biodegradable material insoluble in water having a high affinity with hydrocarbons, it consequently becomes localized in contact with the polluting substances and avoids the microorganisms and/or nutrient substances from being rapidly dispersed in the environment without being able to exert their function, for example due to the motion of waves and currents present in bodies of water such as seas (coastal and/or pelagic), lakes or rivers.

Poly-hydroxyalkanoates (PHAs) are polymers produced by microorganisms isolated from natural environments or also by genetically modified microorganisms, which act as carbon and energy reserves and which are accumulated by various species of bacteria under unfavourable growth conditions and in the presence of an excess carbon source. PHAs are synthesized and accumulated by about 300 different microbial species, included within more than 90 kinds of Gram-positive and Gram-negative bacteria, such as, for example, *Bacillus, Rhodococcus, Rhodospirillum, Pseudomonas, Alcaligenes, Azotobacter, Rhizobium*. In cells, PHAs are stored in the form of microgranules, whose size and number per cell varies in the different bacterial species.

In general, PHAs are polymers containing repetitive units having the formula

$$-O-CHR_1-(CH_2)_n-CO-\qquad(I)$$

wherein:
$R_1$ is selected from: —H, $C_1$-$C_{12}$ alkyls, $C_4$-$C_{16}$ cycloalkyls, $C_2$-$C_{12}$ alkenyls possibly substituted by at least one group selected from: halogen (F, Cl, Br), —CN, —OH, —COOH, —OR, —COOR (R=$C_1$-$C_4$ alkyl, benzyl);
n is zero or an integer ranging from 1 to 6, and is preferably 1 or 2.

Preferably, $R_1$ is methyl or ethyl, and n is 1 or 2.

PHAs can be either homopolymers or copolymers or terpolymers. In the case of copolymers or terpolymers, these can consist of different repetitive units having formula (I), or at least one repetitive unit having formula (I) in combination with at least one repetitive unit deriving from co-monomers capable of co-polymerizing with hydroxy-alkanoates, for example lactones or lactams. In the latter case, the repetitive units having formula (I) are present in a quantity equal to at least 10% by moles with respect to the total moles of the repetitive units.

Particularly preferred repetitive units having formula (I) are those deriving from: 3-hydroxybutyrate, 3-hydroxyvalerate, 3-hydroxyhexanoate, 3-hydroxyoctanoate, 3-hydroxyundec-10-enoate, 4-hydroxyvalerate.

PHAs can be divided into three groups, in relation to the number of carbon atoms forming the monomeric unit: PHAscls (short chain length) are composed of monomeric units having from 3 to 5 carbon atoms, PHAmcls (medium chain length) are composed of monomeric units having from 6 to 15 carbon atoms, whereas PHAlcls (long chain length) are composed of monomeric units having more than carbon atoms. PHAscls have a high degree of crystallinity, whereas PHAmcls and PHAlcls are elastomers with a low crystallinity and have a low melting point.

Particularly preferred PHAs are: poly-3-hydroxybutyrate (PHB), poly-3-hydroxyvalerate (PHV), poly-3-hydroxyhexanoate (PHH), poly-3-hydroxyoctanoate (PHO), poly(3-hydroxybutyrate-co-3-hydroxyvalerate) (PHBV), poly(3-hydroxybutyrate-co-3-hydroxyhexanoate) (PHBH), poly(3-hydroxybutyrate-co-4-hydroxybutyrate), poly(3-hydroxyoctanoate-co-3-hydroxyundecen-10-enoate) (PHOU), poly(3-hydroxybutyrate-co-3-hydroxyvalerate-co-4-hydroxyvalerate (PHBVV), or mixtures thereof.

PHAs preferably have a weight average molecular weight ($M_w$) ranging from 5,000 to 1,500,000 Da, more preferably from 100,000 to 1,000,000 Da. The weight average molecular weight can be determined according to known techniques, in particular by means of GPC (Gel Permeation Chromatography) analysis.

As far as the production of PHAs is concerned, this is preferably obtained by microbial fermentation of an organic substrate (for example, carbohydrates or other fermentable substrates, such as glycerol) by means of a strain of microorganisms capable of producing PHAs, and the subsequent recovery of the PHAs from the cell mass. For further details, reference should be made, for example, to patent applications WO 99/23146, WO 2011/045625 and WO 2015/015315. Substrates suitable for the production of PHAs via fermentation can be obtained in particular from the processing of vegetables, for example juices, molasses, pulp from sugar beet processing, sugar cane. These substrates generally contain, in addition to sucrose and other carbohydrates, organic growth factors, nitrogen, phosphorous and/or other minerals useful as nutrients for cell growth. An alternative consists of glycerol, a low-cost organic carbon source, as it is a by-product of the production of biodiesel (see for example U.S. Pat. No. 8,956,835 B2).

For the implementation of the present invention, the PHA is advantageously used in the form of particles, so as to increase the exchange surface with the environment and therefore the bioremediation effect. The particles preferably have an average size ranging from 0.1 µm to 1,000 µm, more preferably from 1 µm to 500 µm. These dimensions can be determined according to techniques well known in the art, such as particle-size detection systems in suspension with laser detectors, known as Dynamic Light Scattering (DLS) techniques (see the standard ISO 13320-2009). As an alternative, electron microscope images can be used (SEM) which are processed by means of digital analysis.

Alternatively, the PHA can be used in other forms, for example elements having forms that can increase the exchange surface with the environment and favour floating or contact with the hydrocarbons dispersed in the waters, for example perforated panels, hollow tiles, and the like. These elements can be obtained by moulding, extrusion or other methods well known for the processing and forming of plastic materials.

If microorganisms capable of metabolizing hydrocarbons are included in the PHA, these can be included in the polymer in such a quantity as to obtain a concentration of vital cellular units (Unit Forming Colony, (UFC)) preferably from $10^3$ to $10^{10}$ per gram of PHA, more preferably from $10^5$ to $10^8$ per gram of PHA.

There are numerous species of microorganisms capable of metabolizing hydrocarbons, which are generally bacteria, but also fungi or yeasts. They are stimulated by the presence of PHA under aerobic conditions, which are guaranteed by the oxygen naturally dissolved in waters.

In particular, the aerobic bacteria can be divided into:

(a) oil-eating bacteria (BICs), which are capable of completely metabolizing hydrocarbons until water and carbon dioxide are obtained; and (b) hydrocarbon-degrading bacteria, which are only capable of degrading hydrocarbons having smaller molecules, without reaching the formation of water and carbon dioxide.

Oil-eating bacteria can belong, for example, to the following species:
*Alcanivorax*
*Cycloclasticus*
*Oleiphilus*
*Oleispira*
*Thalassolituus*

Hydrocarbon-degrading bacteria can belong, for example, to the following species:
*Acinetobacter* (GammaProteobacteria)
*Aeromonas* (GammaProteobacteria)
*Alcaligenes* (BetaProteobacteria)
*Alteromonas* (GammaProteobacteria)
*Arthrobacter* (High GC group)
*Bacillus* (Firmicutes)
*Flavobacterium* (CFB group)
*Georgfuchsia* (BetaProteobacteria)
*Halomonas* (GammaProteobacteria)
*Idiomarina* (GammaProteobacteria)
*Klebsiella* (GammaProteobacteria)
*Labrenzia* (AlphaProteobacteria)
*Marinobacter* (GammaProteobacteria)
*Marinomonas* (GammaProteobacteria)
*Maritimibacter* (AlphaProteobacteria)
*Methylophaga* (GammaProteobacteria)
*Muricauda* (CFB group bacteria)
*Neptunomonas* (GammaProteobacteria
*Novosphingobium* (AlphaProteobacteria)
*Nocardia* (High GC group)
*Oleibacter* (GammaProteobacteria)
*Paracoccus* (AlphaProteobacteria)
*Pelagibacter* (AlphaProteobacteria)
*Porticoccus* (GammaProteobacteria)
*Pseudoalteromonas* (GammaProteobacteria)
*Pseudomonas* (GammaProteobacteria)
*Psycroserpens* (GammaProteobacteria)
*Rheinheimera* (GammaProteobacteria)
*Rhodobacter* (AlphaProteobacteria)
*Rhodococcus* (High GC group)
*Roseobacter* (AlphaProteobacteria)
*Roseovarius* (AlphaProteobacteria)
*Sarcina* (Firmicutes)
*Shewanella* (GammaProteobacteria)
*Sphingomonas* (AlphaProteobacteria)
*Sulfitobacter* (AlphaProteobacteria)
*Thalassospira* (AlphaProteobacteria)
*Vibrio* (GammaProteobacteria).

Particularly preferred microorganisms for metabolically attacking and degrading hydrocarbons are:
*Alcaniviorax* spp (Gram negative, non-sporulating)
*Bacillus* spp (Gram positive, non-sporulating)

*Marinobacter* spp (Gram negative, non-sporulating)
*Neptunomonax* spp (Gram negative, non-sporulating)
*Pseudomonas* spp. (Gram negative, non-sporulating)
*Rhodococcus* spp (Gram positive, non-sporulating).

The microorganisms can be used as single strains or, preferably, as mixtures of different strains (consortia), so as to increase the degradation efficiency of hydrocarbons within a wide range of different environmental conditions.

If nutritive substances are included in the PHA, possibly combined with microorganisms capable of metabolizing hydrocarbons, these are introduced in quantities normally ranging from 0.01 g to 2 g, more preferably from 0.05 g to 1 g, per gram of PHA.

Nutritive substances suitable for the purpose can be selected within a wide range of organic or inorganic products, among which:
boric acid ($H_3BO_3$), citric acid ($C_6H_8O_7$), fumaric acid, ammonium acetate ($CH_3COONH_4$), sodium acetate ($CH_3COONa$), potassium acetate ($CH_3COOK$), ammonium bicarbonate ($NH_4HCO_3$), ammonium bromide ($NH_4Br$), sodium bromide (NaBr), sodium carbonate ($Na_2CO_3$), calcium carbonate ($CaCO_3$), ammonium chlorate ($NH_4ClO_3$), ammonium chloride ($NH_4Cl$), cadmium chloride ($CdCl_2$) ferrous chloride ($FeCl_2$), ferric chloride ($FeCl_3$), ferrous chloride tetrahydrate ($FeCl_2 \cdot 4H_2O$), manganese chloride (II) tetrahydrate ($MnCl_2 \cdot 4H_2O$), magnesium chloride hexahydrate ($MgCl_2 \cdot 6H_2O$), copper chloride (II) dihydrate ($CuCl_2 \cdot 2H_2O$), strontium chloride ($SrCl_2$), zinc chloride ($ZnCl_2$), potassium dichromate ($K_2Cr_2O_7$), ammonium dihydrogen phosphate ($NH_4H_2PO_4$), potassium dihydrogenphosphate ($KH_2PO_4$), sodium dihydrogenphosphate ($NaH_2PO_4$), ammonium fluoride ($NH_4F$), calcium fluoride ($CaF_2$), sodium fluoride (NaF), ammonium phosphate $(NH_4)_3 \cdot PO_4$, potassium phosphate ($K_3PO_4$), sodium phosphate ($Na_3PO_4$), ferric phosphate ($FePO_4$), ferrous phosphate [$Fe_3(PO_4)_2$], ammonium sodium hydrogenated phosphate [$NH_4 \cdot NaHPO_4 \cdot 4H_2O$], ammonium and sodium hydrogenphosphate [$NaNH_4HPO_4 \cdot 4H_2O$], diammonium hydrogenphosphate [$(NH_4)_2$ magnesium $HPO_4$], hydrogenphosphate ($MgHPO_4 \cdot 3H_2O$), potassium hydrogenphosphate ($K_2HPO_4$), sodium hydrogenphosphate ($Na_2HPO_4$), ammonium iodide ($NH_4I$), potassium iodide (KI), aluminum nitrate [$Al(NO_3)_3$], ammonium nitrate ($NH_3NO_3$), calcium nitrate [$Ca(NO_3)_2$], lead nitrate [$Pb(NO_3)_2$], potassium nitrate ($KNO_3$), sodium nitrate ($NaNO_3$), strontium nitrate [$Sr(NO_3)_2$], tallium nitrate ($TlNO_3$) zinc nitrate [$Zn(NO_3)_2$] nitrite of ammonium ($NH_4NO_2$), potassium nitrite ($KNO_2$), sodium nitrite ($NaNO_2$), diammonium oxalate [$(NH_4)_2C_2O_4$], ferric oxide ($Fe_2O_3$), ammonium perchlorate ($NH_4ClO_4$), potassium permanganate ($KMnO_4$), ammonium peroxydisulfate [$(NH_4)_2S_2O_8$], ammonium sulfate [$(NH_4)_2SO_4$], potassium chromium sulfate dodecahydrate [$CrK(SO_4)_2 \cdot 12H_2O$], potassium sulfate ($K_2SO_4$), sodium sulfate ($Na_2SO_4$), ferric sulfate [$Fe_2(SO_4)_3$], ferrous sulfate ($FeSO_4$), magnesium sulfate ($MgSO_4$), copper (II) sulfate pentahydrate ($CuSO_4 \cdot 5H2O$), zinc sulfate ($ZnSO_4$), ammonium sulfite [$(NH_4)_2SO_3$], zinc sulfite ($ZnSO_3$), ammonium sulfide [$(NH_4)_2S$], potassium sulfide ($K_2S$), ferric sulfide ($Fe_2S_3$), ferrous sulfide (FeS), sodium sulfide ($Na_2S$), urea ($CH_4N_2O$), or mixtures thereof.

The nutritive substances can obviously be included individually or, preferably, mixed with each other, so as to obtain a composition more suitable for favouring the growth of microorganisms.

Among the nutritive substances, the following are particularly preferred for favouring the growth of microorganisms capable of metabolically attacking hydrocarbons:
ammonium chloride ($NH_4Cl$), sodium nitrate ($NaNO_3$), potassium phosphate ($K_3PO_4$), potassium dihydrogen phosphate ($KH_2PO_4$), sodium dihydrogen phosphate ($NaH_2PO_4$), ferrous chloride tetrahydrate ($FeCl_2 \cdot 4H_2O$), urea ($CH_4N_2O$), or mixtures thereof.

The quantity of nutritive substances added to the waters to be bioremediated is such as to obtain a concentration preferably ranging from 0.01 g to 100 g, more preferably from 0.5 g to 50 g, per litre of contaminated water or soil.

The PHA preferably also comprises at least one surfactant. The addition of a surfactant has the main purpose of favouring the dispersion of the hydrocarbons in the form of microdroplets, thus favouring the attack of the microorganisms thanks to the improved surface/volume ratio. The surfactant can be selected within a wide range of products, in particular from the safest products from an environmental point of view, and which are capable of favouring the growth of microorganisms. Among these: glycolipids (in particular ramnolipids, soforolipids, trealolipids), lipoproteins and lipopeptides, fatty acids, possibly ethoxylated, phospholipids, are particularly preferred.

Said at least one surfactant is preferably present in the composition in a quantity generally ranging from 0.01 g and 2 g, more preferably from 0.05 g to 1 g, per gram of PHA.

The quantity of surfactant added to the waters to be bioremediated is such as to obtain a concentration preferably ranging from 0.01 g to 100 g, more preferably from 0.5 g to 50 g, per litre of contaminated water or soil.

The preparation of the composition according to the present invention can be effected according to known techniques, for example by means of closed or open mixers, operating batchwise or in continuous, without using any particular precautions, provided process temperatures are used which do not cause even a partial degradation of the materials used. In particular, when nutritive substances are included in the composition based on PHA, the process temperature is kept at a value equal to or lower than 120° C., whereas if microorganisms are englobed in the PHA, the process temperature is preferably equal to or lower than 60° C., as higher temperatures can cause a significant reduction in the vitality of the microorganisms themselves.

For the preparation of the composition according to the present invention, it is advantageous to use the aqueous suspension of PHA obtained directly from the bacterial fermentation process which produces PHA itself, without having to precipitate and dry it. The aqueous suspension obtained directly from the production process has optimal characteristics in terms of homogeneity, dispersion and particle size of PHA. The aqueous suspension of PHA obtained from the fermentation process is in any case preferably previously subjected to a purification and whitening step, in order to eliminate residues and substances present in the fermentation broth.

As far as the quantity of PHA to be added and dispersed in the contaminated waters is concerned, this is mainly pre-determined in relation to the type and entity of the pollution to be treated, and can therefore vary within wide limits. The quantity of PHA added to the waters to be bioremediated is generally such as to obtain a concentration preferably ranging from 0.01 g to 1,000 g, more preferably from 0.5 g to 200 g per litre of contaminated water.

The following embodiment examples are provided for purely illustrative purposes of the present invention and should not be considered as limiting the protection scope defined by the enclosed claims.

EXAMPLE 1

A suspension of polyhydroxybutyrate (PHB) in water was collected directly from the purification process of the culture broth in which the polymer had been produced by means of bacterial fermentation on sugar beet molasses. The weight average molecular weight of PHB (determined via GPC) was about 950 kDa. The suspension contained 190 g of PHB per litre of suspension.

The PHA suspension was subjected to a drying process by means of spray-drying at a temperature of 230° C.

The final product was a powder of PHB with an apparent density of 0.35÷0.45 kg/L and an average particle size equal to 20-30 µm. The moisture content was lower than 1%. The product was ready for bagging and direct use.

EXAMPLE 2

A suspension of polyhydroxybutyrate (PHB) in water was collected directly from the purification process of the culture broth in which the polymer had been produced by means of bacterial fermentation on sugar beet molasses. The weight average molecular weight of PHB (determined via GPC) was about 800 kDa. The suspension contained 120 g of PHB per litre of suspension.

A mixture of nutritive substances was added to the PHA suspension, consisting of an aqueous solution of mineral salts thus composed:

ammonium chloride ($NH_4Cl$) 80 g/L, potassium dihydrogenphosphate ($KH_2PO_4$) 8 g/L, sodium nitrate ($NaNO_3$) 20 g/L.

The PHA suspension containing the above mixture was subjected to a drying process by means of spray-drying at a temperature of 220° C.

The final product was a powder containing PHB and mineral salts, with an apparent density of 0.25÷0.35 kg/L and an average particle size equal to 20-30 µm. The moisture content was lower than 1%. The product was ready for bagging and direct use.

EXAMPLE 3

A suspension was prepared of poly-(3-hydroxybutyrate-co-3-hydroxyvalerate-co-4-hydroxyvale-rate (PHBVV) in water starting from the polymer in powder form, having a weight average molecular weight (determined by GPC) of about 500 kDa. The suspension contained 90 g of PHBVV per litre of suspension.

A mixture of bacteria consisting of *Alcanivorax* sp., *Marinobacter* sp., *Sphingongomonas* sp., *Rhodococcus* sp., *Bacillus* sp. was added to the PHBVV suspension. The various bacterial species, in spore, vegetative and/or quiescence form, were inserted at a concentration of about 106 cell bodies per gram of PHBVV present in suspension.

The suspension of PHBVV containing the above mixture was subjected to an orthogonal filtration process, obtaining a cake having 35% of moisture. The cake thus obtained was subjected to a drying process using a bed-dryer at a temperature of 60° C.

The product thus obtained, containing PHBVV and the bacterial mixture, was in powder form with an apparent density of 0.55÷0.65 kg/L. The moisture content was lower than 0.8%. The product was ready for bagging and subsequent direct use.

EXAMPLE 4

In order to verify the effectiveness of the materials prepared according to Examples 1 and 2 in a bioremediation process, a microscale experiment was carried out on a volume of seawater to which a volume of oil was added as described hereunder.

The following products were introduced into a tank having dimensions of 78 cm×33 cm×42 cm (total volumetric capacity equal to 108 L):

a) 90 L of coastal seawater; in order to favour the elimination of metazoans, particulate and/or debris possibly present, the water, before being introduced into the tank, was filtered on a filter having a porosity equal to 300 µm:

b) 45 mL of oil Dansk Blend Crude Oil (gravity API: 33.50).

The content of the tank was kept in motion by means of an internal pump, with recycling equal to 5 L/hr, which allowed a non-turbulent stirring to be maintained. The system also included an "overflow" system and a continuous charge of seawater (1 L/hr) in order to guarantee continuous replacement and simulate the conditions present in a marine environment.

Treatment with PHB alone (OIL-PHA) After the oil had been introduced, 51 g of PHB, prepared according to Example 1, were dispersed in the tank. The powder was distributed homogeneously on the surface in correspondence with and on the oil stain. The PHB powder showed a marked tendency to adhere to the oil, forming lumps which partially tended to precipitate. The recirculating system, however, allowed the lumps of PHB to remain in suspension.

A representative sample was collected at regular time intervals, and the following parameters were measured:

measurement of the total bacterial abundance (DAPI count): the direct cell count was effected with an epifluorescence microscope after colouring with a specific fluorochrome, according to the standard method described in the publication of APAT and IRSA-CNR "Analytical methods for water" 29/2003, chapter 9040 (pages 1149-1153); the values are expressed as logarithm of the number of cells per mL of sample;

measurement of the quantity of residual hydrocarbons with respect to the initial quantity (weight %), measured by means of ionizing flame gas-chromatography (GC-FID).

Figure 2:
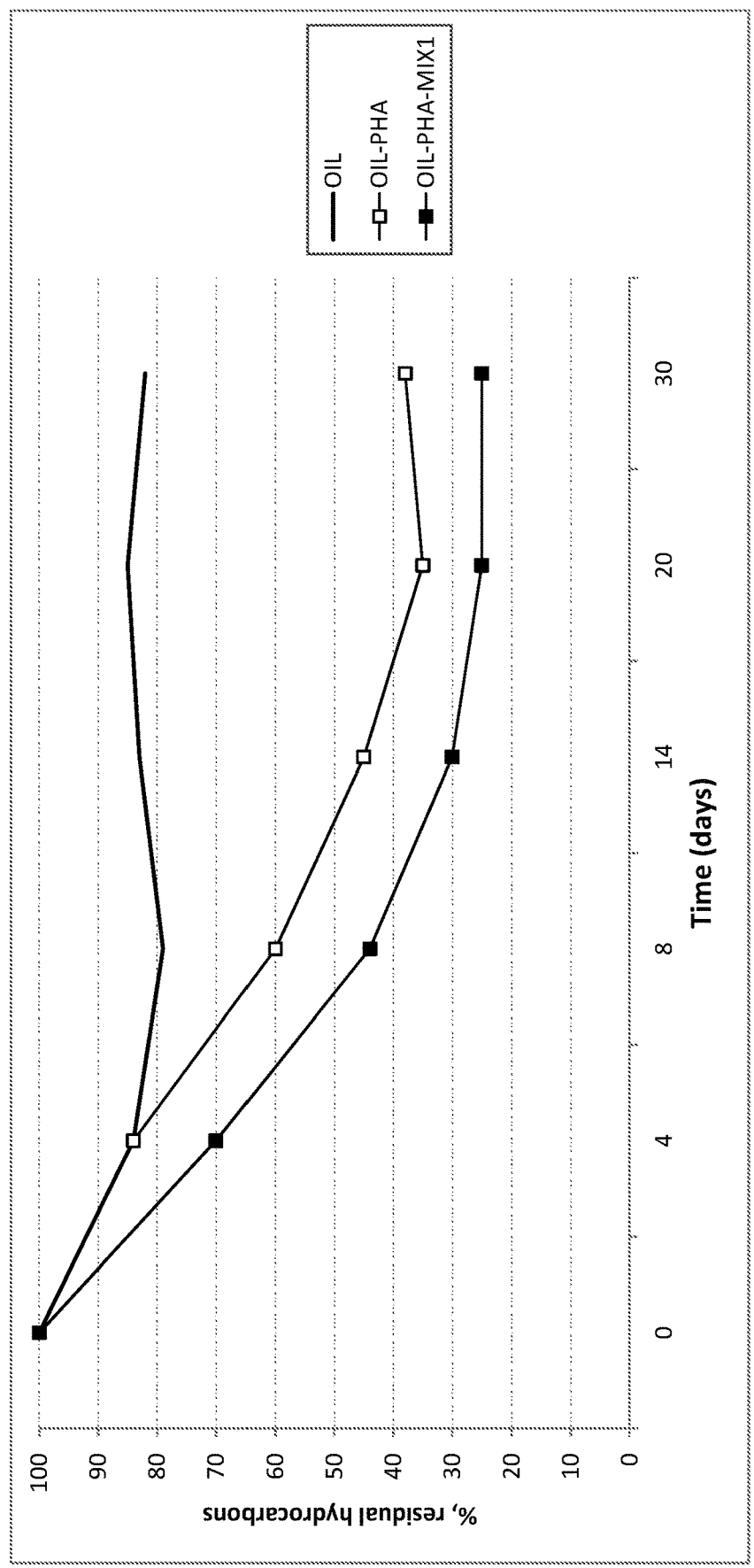

The results are indicated in the graphs of FIGS. 1 and 2. FIG. 1 also shows the value of the microbial abundance present in seawater as such (NSW, natural seawater).

As can be seen in these graphs, with respect to the time zero of the experiment, starting from the fourth day, an increase was observed in the quantitative values (abundance) of the natural microbial population, presumably due to the presence of PHB. At the same time, a significant reduction in the quantity of hydrocarbons was observed, correlated with the beginning of the biodegradation processes attributed to the metabolic activity of the hydrocarbon-degrading bacterial flora. This activity continued until the end of the experimentation period (30 days), when the total abatement proved to be equal to about 60%, whereas the degradation peak (about 65%) was observed on the $20^{Th}$ day of experimentation (FIG. 2).

Treatment with PHB and nutritive substances (OIL-PHA-MIX1).

The experiment was carried out according to the same operative procedures described above, using, instead of PHB alone as in Example 1, a composition consisting of PHB and nutritive substances prepared according to Example 2, which was added in a quantity of 100 g.

The results are indicated in FIGS. 1 and 2, in which a trend of the DAPI count and abatement of hydrocarbons substantially analogous to the OIL-PHA case, can be observed, with slightly improved values (hydrocarbon abatement equal to about 70% already after 14 days).

For comparative purposes, the same experiment was carried out without the addition of PHB and/or nutritive substances, i.e. pouring only OIL into the tank. The results are also indicated in FIGS. 1 and 2, from which the improvement in terms of abatement of hydrocarbons due to the addition of PHB or PHB and nutritive substances, is evident.

The invention claimed is:

1. A method for bioremediation of waters contaminated with hydrocarbons, the method comprising:
    putting the contaminated waters in contact with at least one polyhydroxyalkanoate (PHA); and
    allowing microorganisms, present in the contaminated waters and capable of metabolizing the hydrocarbons, to develop and degrade the hydrocarbons under an aerobic condition;
    wherein the at least one PHA is dispersed in the contaminated waters in a form of particles,
    wherein the particles have an average size greater than or equal to 0.1 micron ($\mu m$) and less than or equal to 1,000 $\mu m$, and
    wherein the at least one PHA in the form of the particles is dispersed in the contaminated waters without the addition of other substances that stimulate metabolic activity of the microorganisms.

2. The method of claim 1, wherein the at least one PHA is selected from: poly-3-hydroxybutyrate (PHB), poly-3-hydroxyvalerate (PHV), poly-3-hydroxyhexanoate (PHH), poly-3-hydroxyoctanoate (PHO), poly(3-hydroxybutyrate-co-3-hydroxyvalerate) (PHBV), poly(3-hydroxybutyrate-co-3-hydroxyexanoate) (PHBH), poly(3-hydroxybutyrate-co-4-hydroxybutyrate), poly(3-hydroxyoctanoate-co-3-hydroxyundecen-10-enoate) (PHOU), poly(3-hydroxybutyrate-co-3-hydroxyvalerate-co-4-hydroxyvalerate (PHBVV), or mixtures thereof.

3. The method of claim 1, wherein the at least one PHA is added to the contaminated waters in an amount so as to obtain a concentration greater than or equal to 0.01 gram (g) per liter of the contaminated waters and less than or equal to 1,000 g per liter of the contaminated waters.

4. The method of claim 1, wherein the particles are in a form of powder or microgranules.

5. The method of claim 1, wherein the particles have an average size greater than or equal to 1 micron ($\mu m$) and less than or equal to 500 $\mu m$.

6. A method for bioremediation of waters contaminated with hydrocarbons, the method comprising:
    preparing an aqueous suspension of at least one polyhydroxyalkanoate (PHA);
    putting the contaminated waters in contact with the aqueous suspension; and
    allowing at least one first microorganism, present in the contaminated waters and capable of metabolizing the hydrocarbons, to develop and degrade the hydrocarbons under an aerobic condition;
    wherein the at least one PHA is dispersed in the aqueous suspension in a form of particles, and
    wherein the particles have an average size greater than or equal to 0.1 micron ($\mu m$) and less than or equal to 1,000 $\mu m$.

7. The method of claim 6, wherein the at least one PHA comprises at least one nutritive substance suitable for promoting development of the at least one first microorganism.

8. The method of claim 7, wherein the at least one nutritive substance is selected from: ammonium chloride ($NH_4E_1$), sodium nitrate ($NaNO_3$), potassium phosphate ($K_3PO_4$), potassium dihydrogen phosphate ($KH_2PO_4$), sodium dihydrogen phosphate ($NaH_2PO_4$), ferrous chloride tetrahydrate ($FeCl_2 \cdot 4H_2O$), urea ($CH_4N_2O$), or mixtures thereof.

9. The method of claim 7, wherein the at least one nutritive substance is added to the contaminated waters in an amount so as to obtain a concentration greater than or equal to 0.01 grams (g) per liter of the contaminated waters and less than or equal to 100 g per liter of the contaminated waters.

10. The method of claim 6, wherein the at least one PHA comprises at least one second microorganism capable of metabolizing the hydrocarbons.

11. The method of claim 6, wherein the at least one PHA comprises at least one surfactant.

12. A method for bioremediation of waters contaminated with hydrocarbons, the method comprising:
    preparing at least one polyhydroxyalkanoate (PHA);
    putting the contaminated waters in contact with the at least one PHA; and
    allowing at least one first microorganism, present in the contaminated waters and capable of metabolizing the hydrocarbons, to develop and degrade the hydrocarbons under an aerobic condition;
    wherein the at least one PHA comprises at least one second microorganism, capable of metabolizing the hydrocarbons, englobed in the at least one PHA,
    wherein the at least one PHA is dispersed in the contaminated waters in a form of particles, and
    wherein the particles have an average size greater than or equal to 0.1 micron ($\mu m$) and less than or equal to 1,000 $\mu m$.

13. The method of claim 12, wherein the at least one second microorganism comprises one or more bacteria, one or more fungi, or one or more yeasts.

14. The method of claim 12, wherein the at least one second microorganism comprises one or more oil-eating bacteria or one or more hydrocarbon-degrading bacteria.

15. The method of claim 12, wherein the at least one second microorganism is included in the at least one PHA in an amount so as to obtain a concentration of vital cellular units (Unit Forming Colony, UCF) greater than or equal to $10^3$ per gram of the at least one PHA and less than or equal to $10^{10}$ per grain of the at least one PHA.

16. The method of claim 12, wherein the at least one PHA further comprises at least one nutritive substance suitable for promoting development of the at least one first microorganism.

17. The method of claim 16, wherein the at least one nutritive substance is selected from: ammonium chloride ($NH_4Cl$)sodium nitrate ($NaNO_3$), potassium phosphate ($K_3PO_4$), potassium dihydrogen phosphate ($KH_2PO_4$), sodium dihydrogen phosphate ($NaH_2PO_4$), ferrous chloride tetrahydrate ($FeCl_2 \cdot 4H_2O$), urea ($CH_4N_2O$), or mixtures thereof.

18. The method of claim 16, wherein the at least one nutritive substance is added to the contaminated waters in an amount so as to obtain a concentration greater than or equal to 0.01 grams (g) per liter of the contaminated waters and less than or equal to 100 g per liter of the contaminated waters.

19. The method of claim 12, wherein the at least one PHA further comprises at least one nutritive substance suitable for promoting development of the at least one first microorganism and the at least one second microorganism.

20. The method of claim 12, wherein the at least one PHA further comprises at least one surfactant.

* * * * *